(12) United States Patent
Yu

(10) Patent No.: US 6,930,222 B2
(45) Date of Patent: Aug. 16, 2005

(54) IN VIVO ANIMAL MODEL OF HUMAN LEUKEMIA

(75) Inventor: John C. Yu, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 311 days.

(21) Appl. No.: 09/935,386

(22) Filed: Aug. 22, 2001

(65) Prior Publication Data

US 2002/0046411 A1 Apr. 18, 2002

Related U.S. Application Data

(60) Provisional application No. 60/325,741, filed on Aug. 22, 2000.

(51) Int. Cl.$^7$ ....................... A01K 67/00; A01K 67/033
(52) U.S. Cl. ................................. 800/10; 800/8; 800/9
(58) Field of Search ................... 800/8, 9, 10; 424/93.1

(56) References Cited

U.S. PATENT DOCUMENTS

| | | | | |
|---|---|---|---|---|
| 5,486,359 A | * | 1/1996 | Caplan et al. .............. | 424/93.7 |
| 5,733,542 A | | 3/1998 | Haynesworth et al. ..... | 424/93.7 |
| 6,010,696 A | | 1/2000 | Caplan et al. .............. | 424/93.7 |

FOREIGN PATENT DOCUMENTS

WO    WO 01/94541 A2    12/2001

OTHER PUBLICATIONS

Blair et al. Blood, 89:3104–3112 (1997).*
Yu, J. et al. Proceedings of the Am. Association for Cancer Research Annual Meeting, Mar. 1999, vol. 40, p. 660, Abstract No. 4352.*
Encyclopedia Brittannica Online, "rodent".*
http://www.taconic.com/anmodels/animlmod.htm, NIH Nude Rat, NOD/scid mouse.*
Dialynas, et al., "Engraftment of Human T–Cell Acute Lymphoblastic Leukemia in Immunodeficient NOD/SCID Mice Which Have Been Preconditioned by Injection of Human Cordl Blood", Stem Cells (Mizmisburg) 19: 443–452 (2001).
Dialynas, et al., "Preconditioning With Fetal Cord Blood Facilitates Engraftment of Primary Childhood T–Cell Acute Lymphoblastic Leukemia in Immunodeficient Mice", Blood 97: 3218–3225 (2001).
Steele, et al., "Growth of Human T–Cell Lineage Acute Leukemia in Severe Combined Immunodeficiency (SCID) Mice and Non–Obese Diabetic SCID Mice", Blood 90: 2015–2019 (1997).
Steele, et al., "T–Cell Acute Lymphoblastic Leukemia (T-ALL):Engraftment in SCID Mice", Blood 86: 782A (1995).

Smith, et al., "Colony Formation in Vitro by Leukemic Cells in Acute Lymphoblastic Leukemia (ALL)", Blood 52: 712–718 (1978).
Smith, et al., "Monoclonal Antibody with Enzymatic Profiles of Human Malignant T–Lymphoid Cells and Derived Cell Lines", Cancer Res. 44: 5657–5660 (1984).
Touw, et al., "Common and Pre–B Acute Lymphoblastic Leukemia Cells Express Interleukin 2 Receptors, and Interleukin 2 Stimulates in vitro Colony Formation", Blood 66: 556–561 (1985).
Touw, et al., "Acute Lymphoblastic Leukemia and Non–Hodgkin's Lymphoma of T Lineage: Colony–Forming Cells Retain Growth Factor (interleukin 2) Dependence", Blood 68: 1088–1094 (1986).
Uckun, et al., "Use of Colony Assays and Anti–T Cell Immunotoxins to Elucidate the Immunobiologic Features of Leukemic Progenitor Cells in T–Lineage Acute Lymphoblastic Leukemia", J. Immunol. 140: 2103–2111 (1998).
Lange, et al., "Growth Factor Requirements of Childhood Acute Leukemia: Establishment of GM–CSF–Dependent Cell Lines", Blood 70: 192–199 (1987).
Gjerset, et al., "Establishment of Continuous Cultures of T–Cell Acute Lymphoblastic Leukemia Cells at Diagnosis", Cancer Res. 50: 10–14 (1990).
Uckun, et al., "Autologous Bone Marrow Transplantation in High–Risk Remission T–Lineage Acute Lymphoblastic Leukemia Using Immunotoxins Plus 4–Hydroperoxycyclophosphamide for Marrow Purging", Blood 76: 1723–1733 (1990).
Terpstra, et al., "Long–Term Leukemia–Initiating Capacity of a CD34 Subpopulation of Acute Myeloid Leukemia", Blood 87: 2187–2194 (1996).
Bonnet, et al., "Human acute myeloid leukemia is organized as a hierarchy that originates from a primitive hematopoietic cell", Nature Med. 3:730–737 (1997).
Kersey, "Fifty Years of Studies of the Biology and Therapy of Childhood Leukemia", Blood 90: 4243–4251 (1997).
Holyoake, et al., "Isolation of a Highly Quiescent Subpopulation of Primitive Leukemic Cells in Chronic Myeloid Leukemia", Blood 94: 2056–2064 (1999).

* cited by examiner

Primary Examiner—Joseph Woitach
Assistant Examiner—Thaian N. Ton
(74) Attorney, Agent, or Firm—Thomas Fitting; Michael J. McCarthy; Thomas E. Northrup

(57) ABSTRACT

The present invention provides a process for making an in vivo model of human leukemia. The process includes the steps of: pre-conditioning an immunodeficient rodent by administering to the rodent a sub-lethal dose of irradiation and injecting the rodent with an effective pre-conditioning amount of human fetal cord blood mononuclear cells; maintaining the rodent for from about 5 to 10 days; and injecting the rodent with an effective engrafting amount of primary human leukemia cells. An in vivo and in vitro model of human leukemia are also provided.

9 Claims, 6 Drawing Sheets

FIG. 2
A: Mouse bone marrow
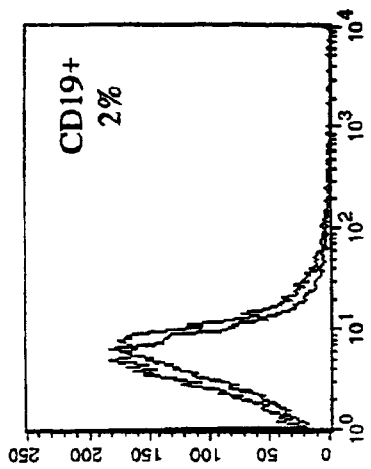
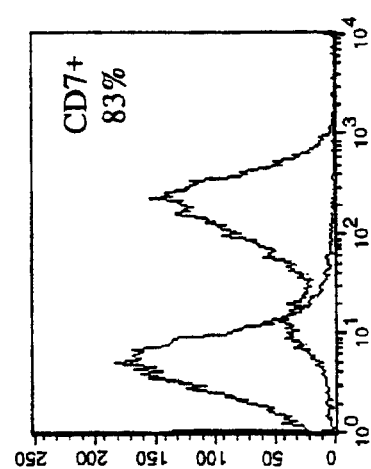
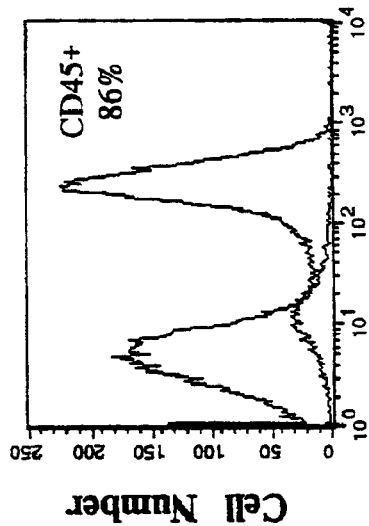
B: Mouse spleen
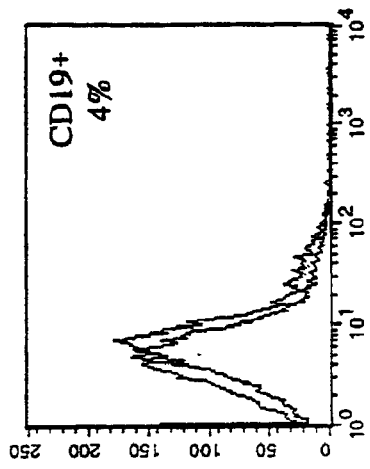
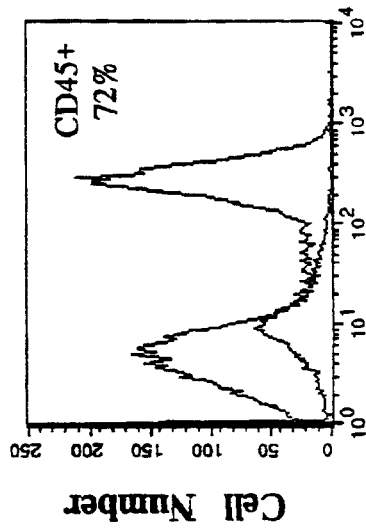

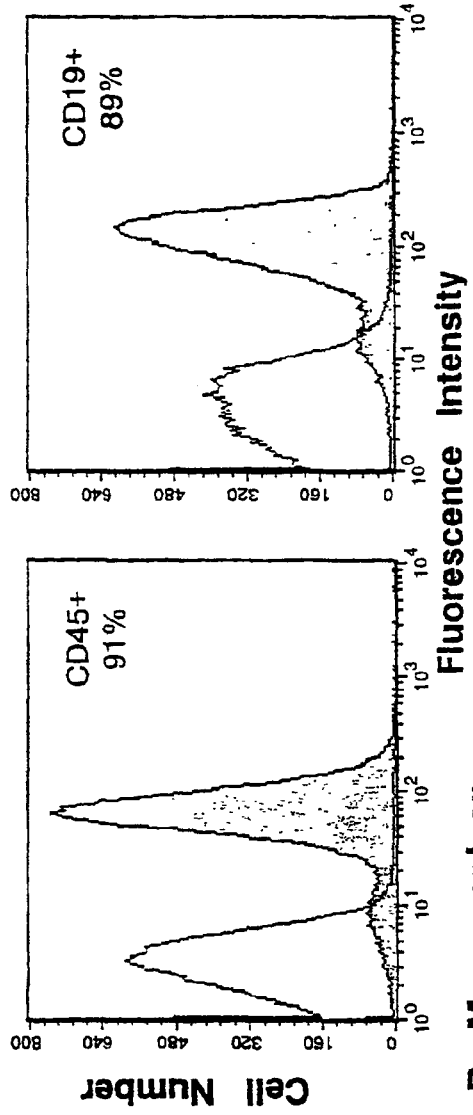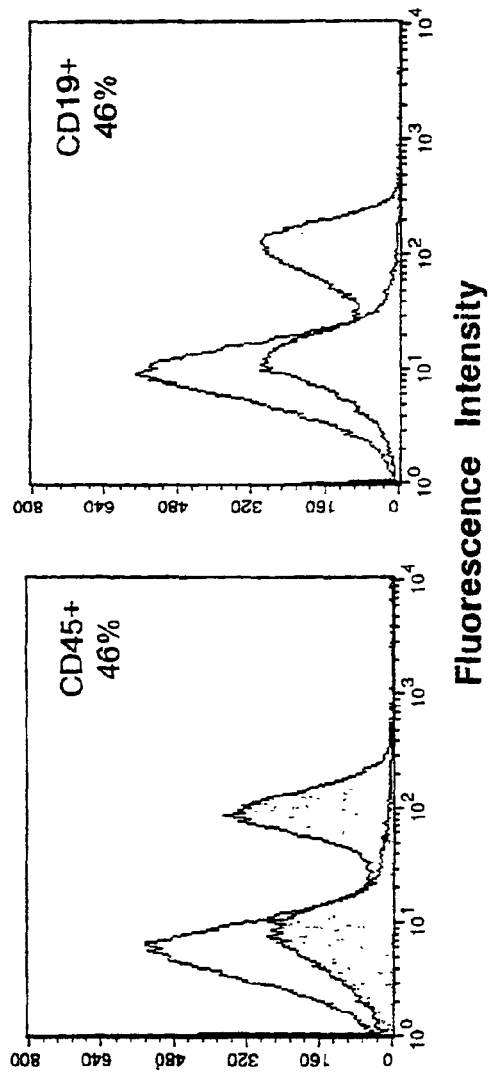
FIG. 6

IN VIVO ANIMAL MODEL OF HUMAN LEUKEMIA

Funds used to support some of the studies reported herein were provided by the National Institutes of Health (NIH DK40218). The United States Government may, therefore, have certain rights in the invention disclosed herein.

TECHNICAL FIELD OF THE INVENTION

The field of this invention is leukemia. More particularly, this invention pertains to models of human leukemia including an in vivo rodent model of human leukemia.

BACKGROUND OF THE INVENTION

T-cell acute lymphoblastic leukemia (T-ALL) comprises ~20% of ALL (Kersey J H., *Blood* 1997; 90: 4243–4251), with ALL being the most common type of cancer in children. A better understanding of the biology of T-ALL at the molecular level would facilitate the development of selective therapy that exploits specific biological properties of the leukemia, thereby improving the outlook for this disease. Even though a number of leukemia cell lines of T-cell origin have been established from patients (Gjerset R, et al., *Cancer Res* 1990; 50: 10–14; Smith S D, et al., *Blood* 1978; 52: 712–718; Lange B, et al., *Blood* 1987; 70: 192–199; and Smith S D, et al., *Cancer Res* 1984; 44: 5657–5660), difficulty in maintaining primary cultures of leukemia cells from patients has impeded study of the development of the disease.

Leukemic progenitor cells have been implicated in the maintenance and expansion of leukemic blast populations (Uckun F M, et al., *Immunology* 1988; 140: 2103–2111; Uckun F M, et al., *Blood* 1990; 76: 1723–1733). These clonogenic blast cells comprise only 0.05 to 1.5% of the bulk marrow or peripheral blood blasts from ALL patients (Uckun F M, et al., *Immunology* 1988; 140: 2103–2111; Touw I, et al., *Blood* 1986; 68: 1088–1094), identified on the basis of their ability to proliferate and form colonies in semi-solid media in response to specific growth factors (Touw I, et al., *Blood* 1986; 68: 1088–1094; Touw I, et al., *Blood* 1985; 66: 556–561). It is generally assumed that the colony-forming blasts represent the in vitro counterparts of the in vivo ALL blast progenitors (Uckun F M, et al., *Immunology* 1988; 140: 2103–2111). Despite these in vitro studies, leukemia-initiating cells were not demonstrated in vivo until recently (Holyoake T, et al., *Blood* 1999; 94: 2056–2064; Ailles LE, et al., *Nat Med* 1997; 3: 730–737; and Terpstra W, et al., *Blood* 1996; 87: 2187–2194).

The ability to engraft T-ALL cells directly from patient samples into immunodeficient rodents such as Nonobese Diabetic x Severe Combined Immunodeficient (NOD/scid) mice would be uniquely valuable in this regard, as well as for predicting the clinical course of the disease, detecting residual disease, and developing individualized therapeutic strategies. The availability of a robust in vivo mouse model for T-ALL would expedite characterization of the corresponding leukemia-initiating cell, as well as delineation of cellular hierarchy within the leukemia. Pre-conditioning sub-lethally irradiated immunodeficient NOD/scid mice with human cord blood mononuclear cells (MNCs) facilitates the subsequent engraftment in these mice of primary T-ALL cells obtained from patients at the time of diagnosis. The present invention provides, in great detail a novel in vivo model of human leukemia engraftment. The data show that the level of engraftment depends on both the number of cord blood MNCs and T-ALL cells injected. In addition, the data document the fidelity of the model to the human pathology with regard to the pattern of leukemia dissemination, as well as with regard to the maintenance of the leukemia-initiating cell within the leukemia-engrafted mouse. The data also provide evidence that the cord blood pre-conditioned NOD/scid mouse is applicable to the study of other human leukemias in addition to T-ALL.

BRIEF SUMMARY OF THE INVENTION

The present invention provides a process for making an in vivo model of human leukemia. The process includes the steps of: pre-conditioning an immunodeficient rodent by administering to the rodent a sub-lethal dose of irradiation and injecting the rodent with an effective pre-conditioning amount of mononuclear cells (MNCs) derived from human fetal cord blood; maintaining the rodent for 3 to 12 days, preferably from about 5 to 10 days and, more preferably from about 6 to 9 days; and injecting the rodent with an effective engrafting amount of primary human leukemia cells. In one embodiment, the cord blood MNCs are stromal cells that comprise mesenchymal stem cells.

The immunodeficient rodent is preferably an immunodeficient mouse, more preferably a NOD/scid mouse. Pre-conditioning the mouse includes two steps. First, the mouse is irradiated with a sub-lethal dose of gamma radiation. The irradiation is whole body irradiation. A preferred sub-lethal radiation dose is from about 200 to about 500 rads. More preferably, the dose is from about 300 to about 400 rads and, even more preferably about 350 rads.

Immediately following irradiation, the mouse is injected with mononuclear cells from fetal cord blood from a normal human subject. A preferred effective number of mononuclear cells is from about $10^6$ to about $10^8$ cells. More preferably, about $10-25 \times 10^6$ cells are injected. About 1 week after pre-conditioning, the mouse is injected with viable primary human leukemia cells. A preferred number of primary leukemia cells is from about $10^6$ to about $10^7$ cells. An especially preferred number of primary leukemia cells is $1-5 \times 10^6$ cells.

In a related aspect, an in vivo model of human leukemia can be produced as set forth above using stromal cells derived from bone marrow. The stromal cells of the bone marrow comprise stem cells of mesenchymal nature. A process of this invention can use any stem cells, especially mesenchymal stem cells, as the pre-conditioning agent. The present invention also provides in vivo models of human leukemia produced by a process of this invention.

In another aspect, the present invention provides an immunodeficient rodent having engrafted human leukemia cells. Preferably, the immunodeficient rodent is an immunodeficient mouse, more preferably is an NOD/scid mouse. The mouse is irradiated, injected with mononuclear cells derived from human fetal cord blood and then injected with human primary leukemia cells. In another aspect of the invention the irradiated mouse is injected with mesenchymal stem cells derived from cord blood or bone marrow and then injected with human primary leukemia cells. The engrafted leukemia cells are found in the bone marrow and spleen of the mouse.

The efficient engraftment and subsequent expansion of the leukemia within pre-conditioned rodents affords a viable window for addressing at the molecular level all events up to and including the expansion. The dissemination of engrafted primary leukemic cells within the pre-conditioned rodent mimics the findings for the human pathology. The level of primary cell engraftment increases both with increasing number of pre-conditioning cells (e.g., MNCs, stem cells) and with increasing number of primary leukemia cells injected.

In a related embodiment, the present invention provides a method of screening anti-cancer drugs. In particular, the screening method can be used to screen anti-leukemia drugs or agents. The method includes the step of administering to the animal model of this invention a putative anti-leukemic agent and monitoring the effects of the drug on the course of leukemia in the model.

BRIEF DESCRIPTION OF THE DRAWINGS

In the drawings that form a portion of the specification

FIG. 2 shows leukemia-engrafted bone marrow and spleen from a cord blood pre-conditioned mouse injected with primary T-ALL cells. Mice were analyzed by flow cytometry for T-ALL engraftment in bone marrow (A) and spleen (B). For each panel, the filled histogram curve corresponds to the indicated experimental monoclonal antibody (mAb) and is superimposed over an open histogram corresponding to the isotype control mAb. The fraction of cells staining positive for the experimental mAb was determined by subtraction of the curves, using CellQuest 3.2.1 software. The percentage of human $CD45^+$, $CD7^+$, and $CD19^+$ cells is indicated in the panels.

FIG. 6 shows the engraftment of primary childhood B-ALL in cord blood pre-conditioned mice. Specifically, mice were injected with $25 \times 10^6$ cord blood MNCs 9 days prior to injection with $5 \times 10^6$ primary B-ALL cells. The mice were sacrificed for analysis 6 weeks after injection of the B-ALL cells. The percentage of engrafted B-ALL in bone marrow (A) and spleen (B) was determined flow cytometrically as $CD45^+CD19^+$ cells.

DETAILED DESCRIPTION OF THE INVENTION

Figure 1:
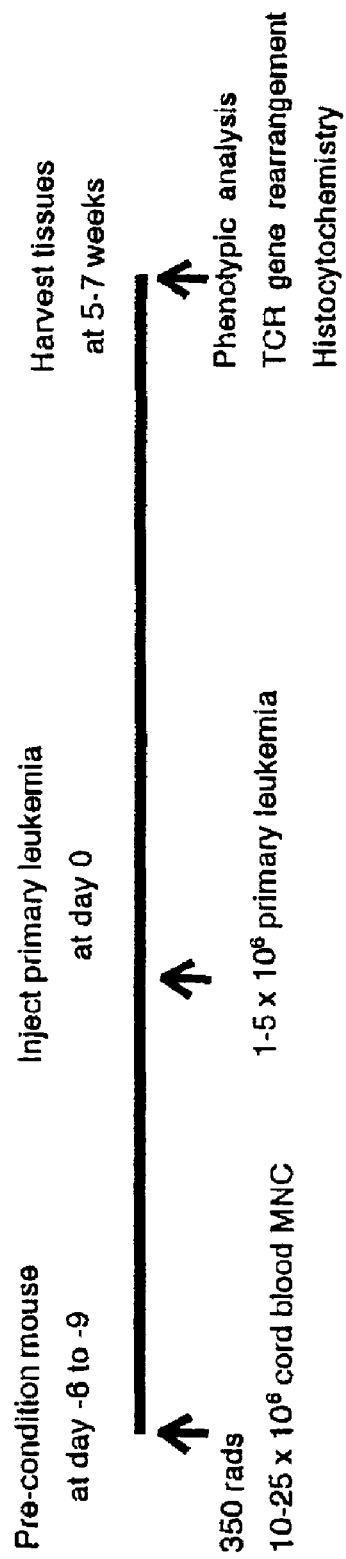
FIG. 1 shows a protocol for cord blood pre-conditioning of NOD/scid mice and analysis of the engraftment of primary human leukemia.

The present invention provides models of leukemia including an in vivo animal model of human leukemia. A preferred animal for use with the in vivo model is a rodent and, more particularly, a mouse. The rodent is immunodeficient. That is, the animal lacks the normal capacity to respond to an insult with an immunological response. Numerous immunodeficient rodent models are well known in the art. An especially preferred immunodeficient animal is a severe combined immunodeficient mouse (scid mouse). Means for obtaining such scid mice are well known in the art. An especially preferred scid mouse for use in the present invention is a Nonobese Diabetic x severe combined immunodeficient (NOD/scid) mouse.

The immunodeficient animal contains engrafted human leukemia cells. As used herein, the term "engrafted" and its grammatical equivalents means transplanted cells that have migrated throughout the organism to particular tissues. Engrafted leukemia cells can be found throughout the animal model. More particularly, engrafted leukemia cells are found in the liver (portal and mesenchymal areas), kidney (perivascular and periglomerular interstitial spaces), lung (parenchymal tissue), thymus, adrenal gland and peripheral blood. The largest number of engrafted cells is found in the hemopoietic tissues, bone marrow and spleen.

An in vivo model of leukemia according to the present invention has a variety of uses. One, the model can be used to study leukemogenesis. Two, the model can serve as a vehicle for testing the efficacy of various treatments. Third, the model can be used as a vehicle for screening putative antileukemia therapeutic agents. Fourth, the model can serve as a mean for continuous expansion of patient's leukemia cells for diagnosis/research purposes.

A detailed description of how to make an in vivo animal model of human leukemia is set forth hereinafter below. NOD/scid mice (Shultz L D, et al., *J. Immunol* 1995; 154: 180–191) were bred and maintained in a specific pathogen-free environment at The Scripps Research Institute vivarium in sterile Micro-Isolator cages and ventilated mouse racks (Lab Products, Seaford, Del.) without antibiotics. Five to six week old mice of either sex (but matched within a given experiment) were used in the present study.

Heparinized peripheral blood or bone marrow samples were obtained from patients with childhood T-ALL who enrolled in protocol #9400 Pediatric Oncology Group. Analogous samples were also obtained from patients with childhood B-cell acute lymphoblastic leukemia (B-ALL) or acute myeloblastic leukemia (AML). In one study, the mononuclear cell (MNC) fraction from peripheral blood/bone marrow was isolated by Ficoll-Paque density gradient separation (Pharmacia, Piscataway, N.J.). The content of lymphoblasts, as determined by Wright stain, was generally >90%. In some cases, MNCs of leukemia samples were cryopreserved and stored in liquid nitrogen before use in the studies. Viability on thawing was generally greater than 80% as determined by trypan blue dye exclusion.

Fetal cord blood samples were obtained from umbilical cord scheduled for discard, according to procedures approved by our Institutional Review Board. After Ficoll- Paque density gradient centrifugation, the MNCs were collected and washed with RPMI 1640 medium containing 2% fetal calf serum (FCS). Cord blood was used for injection as described below.

In a second study the umbilical cord MNCs were placed in culture, where an adherent layer of cells containing mesenchymal stem cells was observed. Human cord blood MNCs were seeded at $1.5 \times 10^6$ cells/ml in 10% fetal calf serum/RPMI 1640 medium and cultured for two weeks with weekly change of medium. Certain of the cells adhered to the culture plates. These adherent cells were evaluated and found to contain mesenchymal stem cells capable of differentiating into various cells, including osteoblasts and adipocytes. These mesenchymal stem cells were isolated and used in pre-conditioning as set forth below.

The protocol for pre-conditioning of NOD/scid mice and analysis of the engraftment of primary human leukemia is outlined in FIG. 1. Prior to leukemia implantation, the mice received 350 rads total body irradiation from a $^{137}CS$ γ-irradiator. Immediately thereafter, $10-25 \times 10^6$ cells were injected in 0.25 ml sterile PBS via tail vein. Six to nine days later, $1-5 \times 10^6$ viable primary leukemia cells from a patient were suspended in 0.25 ml PBS and injected via tail vein. For a given experiment, leukemia cells from a single donor were used for all mice. Experimental mice were typically set up as two to four replicates. Mice were sacrificed when they became moribund with disseminated leukemia or electively between 5 and 7 weeks after the leukemia cell injection. Necropsies were performed, and the burden of leukemia cells in mouse tissues was determined by flow cytometry and histocytochemistry as described below.

Gross examination of various mouse tissues was performed after laparatomy immediately after sacrifice. Multiple tissues from mice (including liver, kidney, lung, and brain) were fixed in aqueous buffered zinc formalin (Z-fix; Anatech, Battle Creek, Mich.), dehydrated, and embedded in paraffin by routine methods. Glass slides with 4 μm tissue sections were prepared and stained with hematoxylin/eosin. The bone marrow of mice was collected from femurs and tibias. A single cell suspension was prepared by gentle pipetting. Spleen cells were collected by gentle dissociation. Red blood cells within the bone marrow and spleen cell suspensions were lysed using buffered ammonium chloride. Cell debris was removed by filtration through a sterile nylon cell strainer (Becton Dickinson, San Jose, Calif.).

Multi-parameter analysis of single-cell suspensions from mouse bone marrow and spleen was carried out using a FACScan flow cytometer (Becton Dickinson). Two-color immunofluorescence was used to identify human leukemia cells. Fluorescein isothiocyanate (FITC)- or phycoerythrin (PE)-conjugated mouse anti-human monoclonal antibodies (mAbs) were obtained from PharMingen (San Diego, Calif.), with the exception of PE-conjugated anti-TCR V β2 (clone MPB2D5, Coulter, Miami, Fla.). The mAbs used in the work presented here include those directed against human CD5 (clone UCHT2), CD7 (M-T701), CD 19 (HIB 19), CD33 (WM53), and CD45 (HI30). During analysis, red blood cells and debris were gated out on the basis of forward angle and 90° side scatter. At least 15,000 events were collected for each sample. Istoype-matched control mAbs [FITC- or PE-conjugated IgGl (clone MOPC021)] were used to determine the appropriate cursor settings for analysis. Using CellQuest 3.2.1 software (Becton Dickinson), data were analyzed and displayed by two-dimensional plots and by one-dimensional histograms.

Pre-conditioning sub-lethally irradiated immunodeficient NOD/scid mice with human cord blood mononuclear cells (MNCs) facilitates the subsequent engraftment in these mice of primary leukemia cells obtained from patients with T-ALL. As outlined in FIG. 1, in this model irradiated NOD/scid mice are injected with human cord blood MNCs approximately 1 week prior to the injection of primary leukemia cells obtained from patients. The mice are then sacrificed approximately 6 weeks later and the level of leukemia cell engraftment determined. A typical profile of T-ALL engrafted mouse bone marrow and spleen, as assessed by flow cytometry, is presented in FIG. 2. CD45 expression is indicative of total human hematopoietic cell engraftment. CD7 is expressed by engrafted human T-ALL. CD 19 is indicative of engrafted human cells of the B cell lineage. For this experiment, $CD45^+CD7^+$ engrafted T-ALL cells comprise approximately 83% of bone marrow and 68% of spleen, as indicated by the corresponding histograms presented in FIG. 2. Notably, there are very few $CD 19^+$ cells (approximately 2% in bone marrow and 4% in spleen) in the T-ALL engrafted mouse, suggesting that expansion of the T-ALL overtakes the expansion of normal $CD 19^+$ cells developing from engrafted cord blood MNCs (Vormoor J, et al., *Blood* 1994; 83: 2489–2497; Hogan C J, et al., *Blood* 1997; 90: 85–96; Kollmann T R, et al., *Immunology* 1994; 91: 8032–8036; Yu J., *I Formos Med Assoc* 1996; 95: 281–293; and Pflumio F, et al., *Blood* 1996; 88: 3731–3740). In some cases, further confirmation that the engrafted cells were derived from the injected primary T-ALL was carried out by analysis of TCR Vβ gene usage. Similar results were obtained from studies using the mesenchymal stem cells, which were shown to enhance the engraftment of human leukemia cells.

Figure 3:
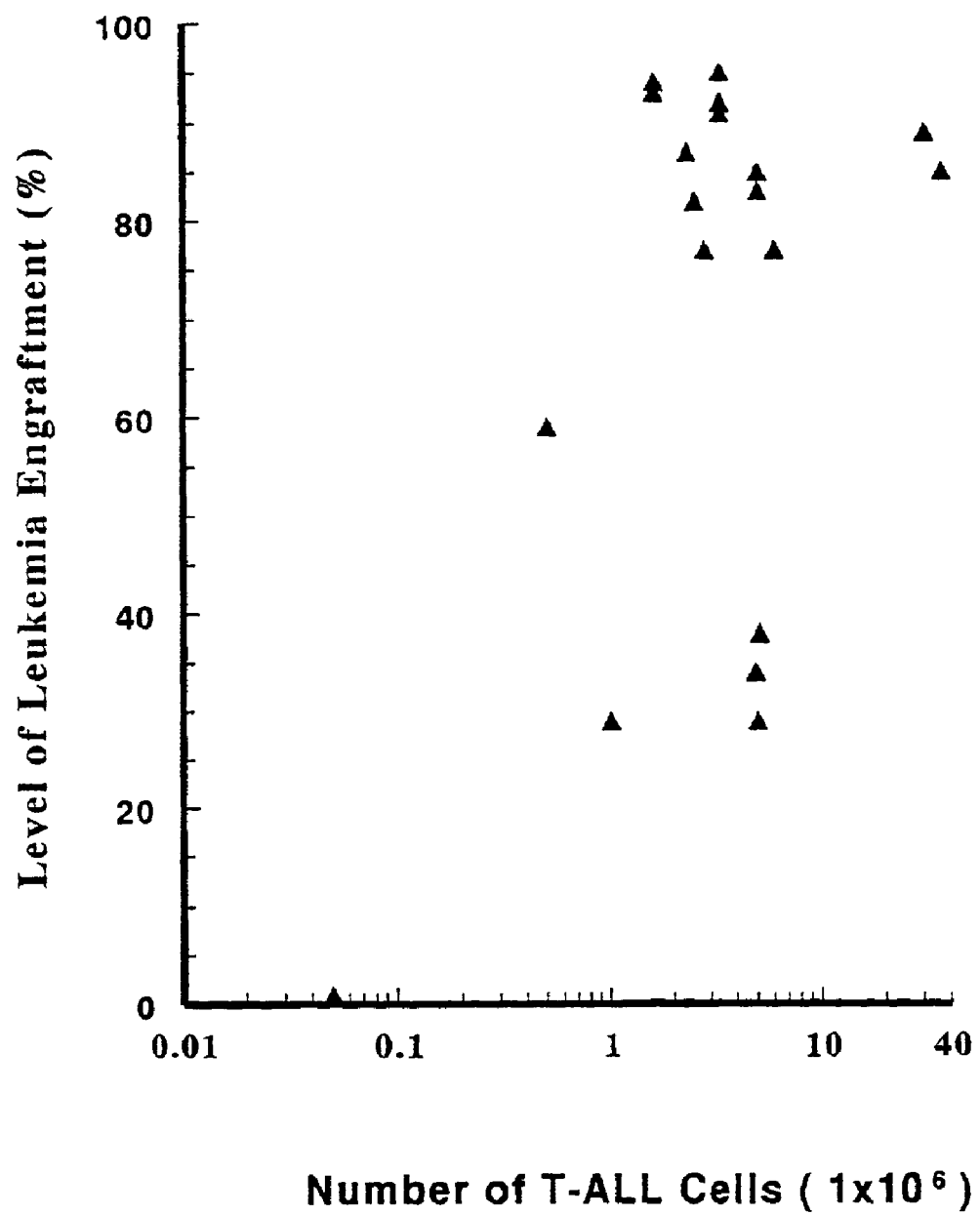
FIG. 3 shows engraftment of primary T-ALL in mouse bone marrow for a series of primary T-ALL donors. The level of T-ALL engraftment was determined by flow cytometry, on the basis of CD45, CD7, and CD5 expression.
Figure 4:
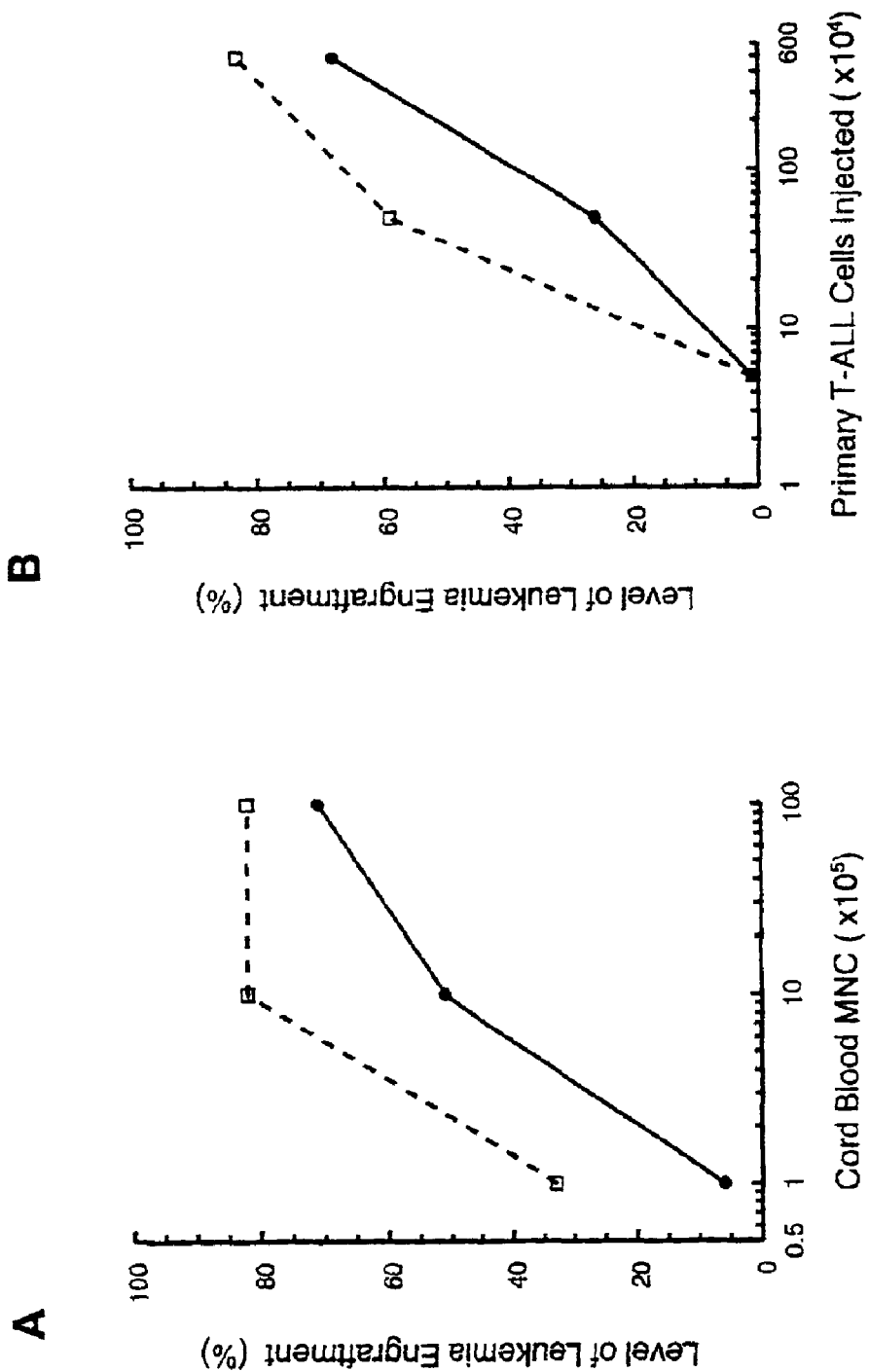
FIG. 4 shows that the level of engraftment in mouse bone marrow and spleen is dependent on both the number of cord blood MNCs and the number of T-ALL cells. In (A), mice were injected with the indicated number of cord blood MNCs 7 days prior to the injection of $2.5 \times 10^6$ primary T-ALL cells; the mice were sacrificed for analysis 6 weeks after injection of the T-ALL cells. In (B), mice were injected with $10 \times 10^6$ cord blood MNCs 7 days prior to the injection of the indicated number of primary T-ALL cells; the mice were sacrificed for analysis 6 weeks after injection of the T-ALL cells. The percentage of T-ALL in engrafted bone marrow (□-□-□) and spleen (●-●-●) was determined flow cytometrically as $CD7^+CD5^+$ cells, the phenotype of the primary T-ALL in each case.

Current studies also characterized the level of T-ALL engraftment in mouse bone marrow for a series of primary T-ALL donors over a range of injected T-ALL cell number (FIG. 3). In these studies, eight different primary T-ALL donors were used. Efficient engraftment in mouse bone marrow typically is observed at 6 weeks following injection of $1-5 \times 10^6$ primary T-ALL cells into a mouse which has been pre-conditioned with cord blood (FIG. 3). Studies then addressed the issue of whether the level of engraftment in mouse bone marrow and spleen at 6 weeks is dependent on the number of cord blood MNCs and the number of primary T-ALL cells injected (FIG. 4). In FIG. 4, two different experiments were set up, with the same primary T-ALL donor but different cord blood donors. From FIG. 4A it is apparent that the level of T-ALL engraftment in mouse bone marrow and spleen at 6 weeks is dependent on the number of cord blood cells used for pre-conditioning. Analogously, from FIG. 4B it is apparent that the level of T-ALL engraftment in bone marrow and spleen at 6 weeks is dependent on the number of primary T-ALL cells injected.

In order to address the likely utility of the present mouse model for the study of T-ALL metastasis and the corresponding therapeutic intervention, the profile of T-ALL dissemination was determined in the engrafted, cord blood pre-conditioned mouse. In liver there were notable infiltrations of leukemia cells in portal and mesenchymal areas. In kidney, human leukemia cells are aggregated in perivascular and periglomerular interstitial spaces. In the lung, leukemia cells were detected within the parenchymal tissue. Engrafted T-ALL cells also disseminated to mouse thymus, adrenal gland, and peripheral blood.

Figure 5:
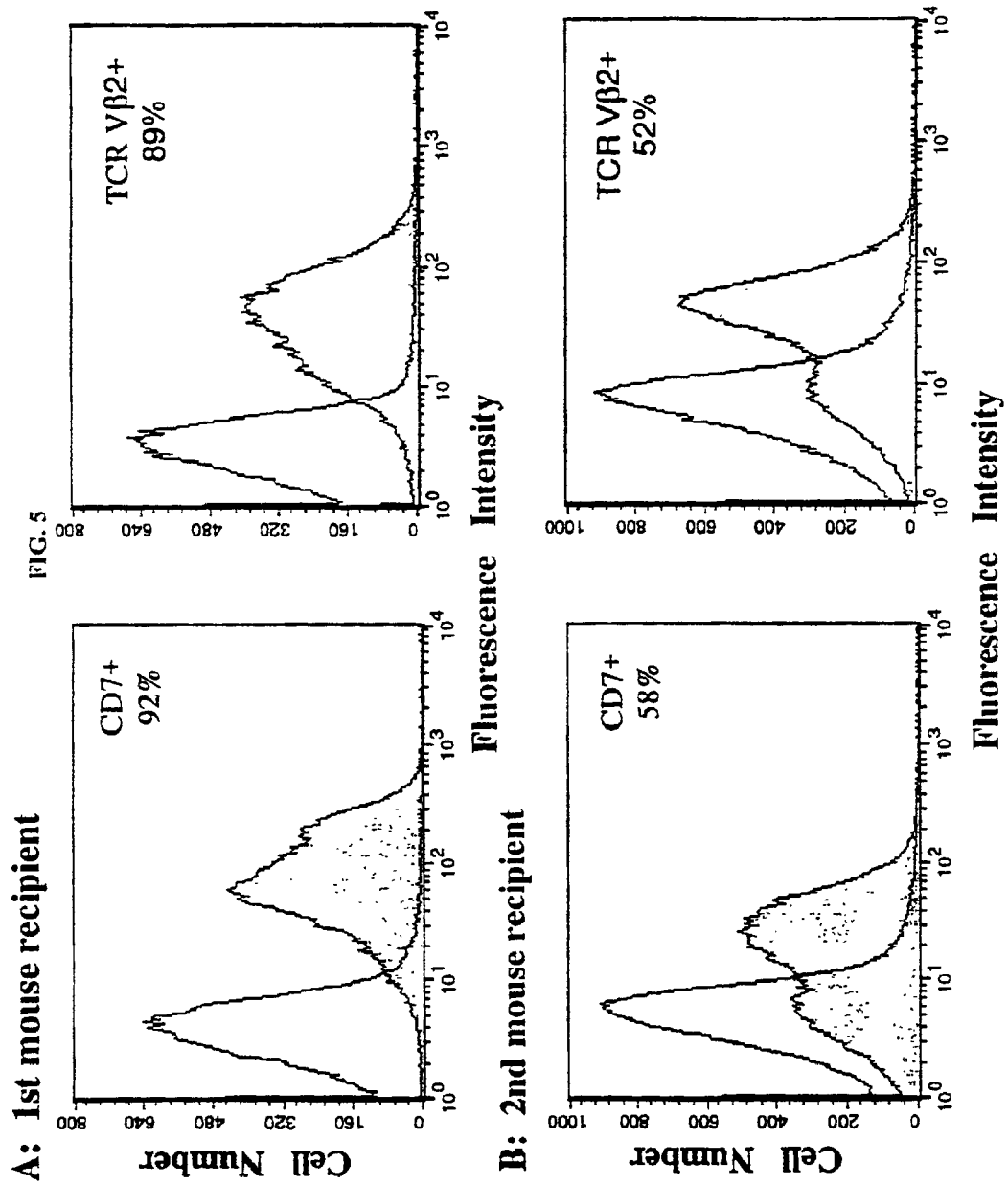
FIG. 5 shows the maintenance of the T-ALL leukemia initiating cell within the leukemia-engrafted mouse. In (A), the first mouse was injected with primary T-ALL cells obtained from a patient. In (B), however, the second mouse was injected with T-ALL cells in engrafted spleen recovered from the mouse in (A). Specifically, in (A) mice were injected with $10 \times 10^6$ cord blood MNCs 9 days prior to the injection of $1.6 \times 10^6$ primary T-ALL cells; the mouse was sacrificed for analysis 7 weeks after injection of the T-ALL cells. In (B) mice were injected with $25 \times 10^6$ cord blood MNCs 8 days prior to the injection of the indicated number of T-ALL cells obtained from engrafted spleen recovered from the mouse in (A); the mouse was sacrificed for analysis 5 weeks after injection of the T-ALL cells. The percentage of T-ALL in engrafted bone marrow was determined flow cytometrically as $CD7^+CD5^+$ and $CD7^+V\beta2^+$ cells. The CD7 and TCR $V\beta2$ profiles are presented here.

Because of its central role in leukemia formation, it was of considerable interest to determine whether in our model system the leukemia-initiating cell was maintained within the leukemia-engrafted mouse and was not, for example, exhausted in the course of T-ALL expansion in vivo. To address this question, it was determined whether T-ALL recovered from the engrafted spleen of a mouse injected with primary T-ALL obtained from a patient could recapitulate the leukemia on transfer to a second, cord blood pre-conditioned mouse. For this work, a primary T-ALL that expresses T cell receptor β chain variable region 2 (TCR Vβ2) was used. In this way, the engrafted T-ALL could be uniquely identified as $CD7^+V\beta2^+$ cells. The results of this experiment are presented in FIG. 5 for mouse bone marrow.

Injection of primary T-ALL cells obtained from the patient into pre-conditioned mice led to high-level engraftment in bone marrow, determined here at 7 weeks after the T-ALL injection (FIG. 5A). Specifically, 92% of the cells in bone marrow expressed CD7 and 89% expressed Vβ2, consistent with the existence of a $CD7^+V\beta2^+$ subset comprising approximately 90% of the bone marrow cells. In the same mouse, $CD7^+V\beta2^+$ cells (T-ALL) accounted for approximately 92% of spleen cells. The T-ALL cells in engrafted spleen were used to inject a second mouse that had been pre-conditioned with cord blood (FIG. 5B). Analysis of this second mouse recipient at 5 weeks after T-ALL injection indicated recapitulation of the leukemia, with 58% of the bone marrow cells expressing CD7 and 52% expressing TCR Vβ2 (consistent with approximately 52% of bone marrow cells having the $CD7^+V\beta2^+$ phenotype). In this second mouse recipient, the level of T-ALL engraflment in spleen ($CD7^+V\beta2^+$ cells) was 68%. These results indicate unambiguously that there is maintenance of the leukemia-initiating cell within the leukemia-engrafted mouse.

Although the model system was developed initially to facilitate study of T-ALL and the pre-clinical testing of associated therapeutic strategies, it was of interest to determine whether it could be applied to the in vivo study of other leukemias. To this end, cord blood pre-conditioned mice were injected with primary childhood B-cell acute lymphoblastoid leukemia (B-ALL) cells and the level of B-ALL engraftment in mouse bone marrow and spleen determined on day 39 after B-ALL injection (FIG. 6). Approximately 90% of mouse bone marrow cells expressed a uniform $CD45^+CD19^+$ human phenotype expected for the engrafted B-ALL. Moreover, 46% of spleen cells expressed the identical $CD45^+CD19^+$ phenotype (FIG. 6B). Preliminary work suggests that the cord blood pre-conditioned mouse may also be applicable to the in vivo study of acute myeloblastic leukemia (AML). In this work, 16% leukemia engraftment in bone marrow and 1% engraftment in spleen were observed for a preconditioned NOD/scid mouse injected 11 days previously with AML.

Enhancement of Leukemia Colony Formation by Cord Blood or Mesenchymal Stem Cell Conditioned Medium in vitro To characterize the nature of the enhancing activity on leukemia engraftment, colony formation of leukemia clonogenic cells was examined in vitro in the presence of cord blood or cord blood derived mesenchymal stem cell conditioned medium. The in vitro leukemia colony assay is based on the ability of leukemic clonogenic cells to proliferate and form colonies in response to growth factors such as IL-2. These leukemic "progenitor" cells have been implicated in the maintenance and expansion of leukemic blast populations.

The leukemia colony formation of primary T-ALL obtained from patients and cultured with 100 units/ml of IL-2 and 10 ng/ml of phorbol 12-myristate 13-acetate (PMA) in methylcellulose was significantly enhanced by the addition of MNC or stem cell conditioned medium, in a dose-dependent manner. The enhancement of T-ALL colony formation is as great as 4-fold by factor(s) present in the conditioned medium was substantially increased compared to that observed in the absence of conditioned medium. On microscopic analysis, there is a wide range of colony sizes in the samples to which conditioned medium was added. The colonies in the cultures were individually picked, pooled for similar sizes of colonies, and the number of leukemia cells counted. It was found that the number of cells per individual colonies in cultures with cord blood conditioned medium ranged from 250 and $285\times10^2$ /colony, as compared to less than 100 cells/colony observed in the absence of conditioned medium. Therefore, this increase in burst size due to the addition of cord blood conditioned medium in the cultures was in the order of several fold to more than 100-fold.

To further confirm that cord blood constitutively expressed in vitro a factor(s), which enhances in vitro leukemia colony formation, a double layer agar assay was performed for leukemia samples. Some "diffusable factor (s)" secreted from irradiated cord blood in the lower agar layer significantly promoted plating efficiency of leukemia colonies in the upper layer in the absence of exogenous IL-2 and PMA. As would be expected, the number of leukemia colonies on day 14 depends both on the number of irradiated cord blood MNCs in the lower agar layer as well as on the number of input TALL cells in the upper agar layer. The absence of colonies when only the irradiated cord blood is cultured indicates that the colonies in the upper layer are derived from the T-ALL preparations.

These in vitro studies of leukemia colony formation show that proliferation of leukemic cells was likely stimulated by the addition of MNC or stem cell conditioned medium. To confirm that the cells recovered from individual colonies in the assay were primarily of leukemic origin and not simply normal T cells from the patient's blood, we took advantage of an atypical surface phenotype of one patient's primary T-ALL. Phenotypic analysis of the primary T-ALL leukemia sample obtained from this patient revealed that these cells are $CD7^+$ (99%), $CD34^+$ (98%), $CD45^+$ (2%) and negative for B cell and monocyte markers. Although these leukemic cells expressed CD7 as expected, they anomalously failed to express CD45 and uniformally expressed CD34. This aberrant phenotype thus permits unambiguous discrimination of the patient's T-ALL cells from normal T cells.

Using this primary leukemia sample, leukemia colony forming assay with the addition of cord blood conditioned medium was performed. It was shown that the addition of cord blood conditioned medium greatly enhanced leukemia colony formation of MNCs from this patient by more than three fold as expected. On day 14, leukemia colonies were individually picked. Approximately $1.4\times10^6$ cells were recovered, and these cells were pooled for flow cytometric analysis. The vast majority of cells are uniquely $CD45^-CD7^+$, $CD45^{-CD}34^+$, and $CD7^+CD34^+$. Collectively, the results are consistent with approximately 90% of the harvested cells from in vitro cultures having the surface phenotype $CD45^-CD7^+CD34^+$, identical to the atypical phenotype of the primary leukemia of this patient. This analysis supports the contention that conditioned medium from cord blood stimulates the in vitro proliferation of primary leukemia cells from patients with T-ALL, rather than simply normal T cells within the primary T-ALL sample obtained from the patient.

Consistent with this, it was further shown by flow cytometry, that the cells from this patient in the upper layer supported by the irradiated cord blood are of leukemia origin and not simply normal T cells from the patient's blood. Specifically, approximately 80% of the harvested cells from the upper layer of the agar assay, were shown to be CD45⁻ CD7⁺ phenotype, similar to the atypical phenotype of primary T-ALL from this patient.

Enhancing activity in cord blood conditioned medium appears to bind to Q Sepharose at pH 7.5 that was eluted at 500 mM NaCl, and to wheat germ agglutinin affinity column that was eluted with 200–300 mM -acetyl-D-glucosamine, and, thus, corresponds to an acidic glycoprotein(s). Cytokine IL-15, a potent immunoregulatory cytokine, is also a T-cell growth factor that can enhance activity of antigen-specific T cells and lymphokine-activated killer cells. It was shown that 10 ng/ml of recombinant IL-15 stimulated colony formation of primary leukemia by about 80% and neutralizing anti-IL-15 antibody (up to 100 ng/ml) was sufficient to block completely the IL-15 induced enhancement of leukemia colony formation in the assay. In contrast, similar doses of neutralizing antibody (10 to 100 ng/ml) did not affect the enhancement attributable to the addition of cord blood conditioned medium in the assay. These results indicate that IL-15 cannot be the leukemia enhancing activity in the cord blood conditioned medium. Consistent with this, determination by ELISA demonstrated that our preparations of cord blood conditioned medium (a total of 22 preparations) contains only a negligible amount of IL-15 (<0.03 ng/ml); and this amount is about 100 times less that the $ED_{50}$ for IL-15 biological activities (i.e., 3 ng/ml).

As the in vitro leukemia colony assay using methylcellulose culture includes the addition of 100 units/ml of IL-2 and 10 ng/ml of PMA, an inducer of IL-2 receptor, the enhancement of leukemia colony formation by cord blood conditioned medium was unlikely to be due simply to an increase in IL-2 or IL-2 receptor. Consistent with this, the amount of IL-2 in the cord blood conditioned medium as determined by ELISA was found to be minimal (approximately at 4.3±3.9 units/ml for four different preparations), as compared to the exogenous IL-2 added in the cultures. Moreover, flow cytometric analysis using anti-IL-2 receptor mAbs (M-A251 for IL-2Rα, 3D7 for IL-2Rβ, and AG184 for IL-2Rγ) indicates that cord blood conditioned medium alone has no effect on the expression of IL-2 receptor.

Mononuclear cells derived from human bone marrow were cultured as described above for cord blood MNCs. The adherent layer, containing mesenchymal stem cells, was isolated as used in both in vitro and in vivo studies as described above. Stem cells derived from bone marrow were found to be effective pre-conditioning agents in the in vivo model of human leukemia and to enhance leukemic colony formation in vitro.

As set forth above, an animal model of the present invention is suitable model of human leukemia. Thus, the model has a variety of uses. One such use is the screening of putative anti-cancer (e.g., anti-leukemic) agents. Such a putative agent is administered to the animal model and the course of leukemia followed over time. Agents can be administered according to any protocol. In addition, the agent can be administered either before or after injection of the primary leukocytes.

What is claimed is:

1. A process for making an in vivo model of human leukemia comprising
    a) pre-conditioning an immunodeficient mouse by administering to the mouse a sub-lethal dose of irradiation and injecting the mouse with an effective pre-conditioning amount of mononuclear cells derived from human fetal cord blood;
    b) maintaining the mouse from step (a) for 5 to 10 days;
    c) injecting the mouse from step (b) with an effective engrafting amount of primary human leukemia cells; and
    d) allowing the primary human leukemia cells to engraft in the mouse to produce the in vivo model of human leukemia.

2. The process of claim 1 wherein the immunodeficient mouse is a NOD/scid mouse.

3. The process of claim 1 wherein administering the sub-lethal dose of irradiation is accomplished by irradiating the mouse with 300 to 400 rads of total body gamma radiation.

4. The process of claim 1 wherein the effective engrafting amount of primary human leukemia cells is from $10^6$ to $10^7$ cells.

5. The process of claim 1 wherein the primary human leukemia cells are T-cell acute lymphoblastic leukemia (T-ALL) cells.

6. The process of claim 1 wherein the effective pre-conditioning amount of human fetal cord blood mononuclear cells is from $10^6$ to $10^8$ cells.

7. The process of claim 1 wherein the mononuclear cells are stem cells.

8. The process of claim 7 wherein the stem cells comprise mesenchymal stem cells.

9. A process for making an in vivo model of human leukemia comprising
    a) pre-conditioning an immunodeficient mouse by administering to the mouse a sub-lethal dose of irradiation and injecting the mouse with an effective pre-conditioning amount of stem cells derived from bone marrow;
    b) maintaining the mouse from step (a) for 5 to 10 days;
    c) injecting the mouse from step (b) with an effective engrafting amount of primary human leukemia cells; and
    d) allowing the primary human leukemia cells to engraft in the mouse to produce the in vivo model of human leukemia.

* * * * *